United States Patent

Ushizawa et al.

[11] Patent Number: 5,190,636
[45] Date of Patent: Mar. 2, 1993

[54] ION-SENSITIVE FILM, METHOD OF PRODUCING THE SAME AND ION SENSOR

[75] Inventors: Norihiko Ushizawa; Shuichiro Yamaguchi; Naoto Uchida; Takeshi Shimomura, all of Nakai, Japan

[73] Assignee: Terumo Kabushiki Kaisha, Tokyo, Japan

[21] Appl. No.: 602,230

[22] PCT Filed: Apr. 25, 1989

[86] PCT No.: PCT/JP89/00434

§ 371 Date: Oct. 24, 1990

§ 102(e) Date: Oct. 24, 1990

[87] PCT Pub. No.: WO89/10554

PCT Pub. Date: Nov. 2, 1989

[30] Foreign Application Priority Data

Apr. 25, 1988 [JP] Japan .................. 63-100161

[51] Int. Cl.$^5$ .................................... G01N 27/26
[52] U.S. Cl. ................................. 204/416; 204/419
[58] Field of Search ............ 435/817; 204/416, 418, 204/419, 153.12, 153.13

[56] References Cited

U.S. PATENT DOCUMENTS

| | | | |
|---|---|---|---|
| 4,214,968 | 7/1988 | Battaglia et al. | 204/416 |
| 4,454,007 | 6/1984 | Pace | 204/416 |
| 4,549,951 | 10/1985 | Knudson et al. | 204/416 |
| 4,753,719 | 6/1988 | Yamaguchi et al. | 204/418 |
| 4,798,664 | 1/1989 | Yamaguchi et al. | 204/416 |
| 4,816,118 | 3/1989 | Oyama et al. | 204/418 |
| 4,839,020 | 6/1989 | Yamaguchi et al. | 204/431 |
| 4,861,454 | 8/1989 | Ushizawa et al. | 204/414 |
| 4,871,442 | 10/1989 | Yamaguchi et al. | 204/418 |
| 4,927,516 | 5/1990 | Yamaguchi et al. | 204/403 |
| 4,968,400 | 11/1990 | Shimomura et al. | 204/403 |

FOREIGN PATENT DOCUMENTS 61-155949 7/1986 Japan .
61-266952 11/1986 Japan .
62-21054 1/1987 Japan .

Primary Examiner—John Niebling
Assistant Examiner—Bruce F. Bell
Attorney, Agent, or Firm—Burns, Doane, Swecker & Mathis

[57] ABSTRACT

The present invention provides an ion sensitive film (6) comprising a mixed layer containing a redox manifesting substance manifesting redox function and a polymeric compound containing an ion carrier substance. The present invention also provides a method of producing the ion sensitive film (6) and an ion sensor which uses the film (6). The ion sensitive film (6) of the present invention enables the provision of an ion sensor having excellent durability, preservative stability and sensor characteristics.

11 Claims, 6 Drawing Sheets

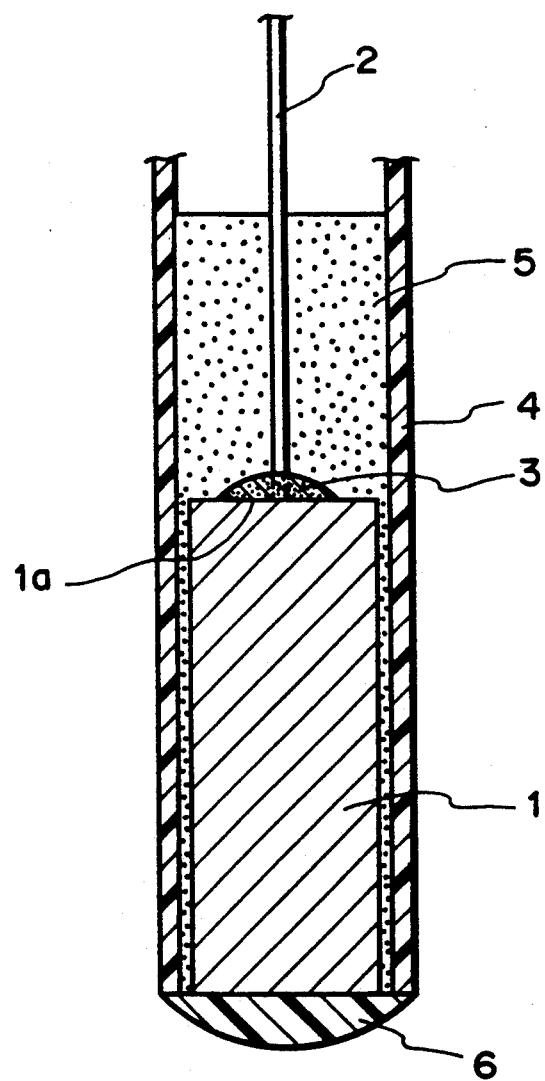
F I G. 1

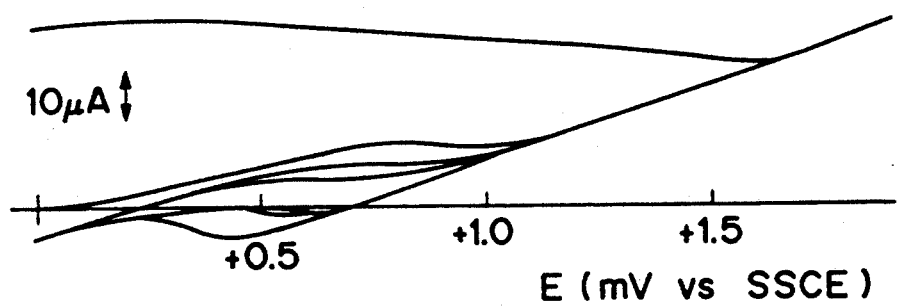
F I G. 2A
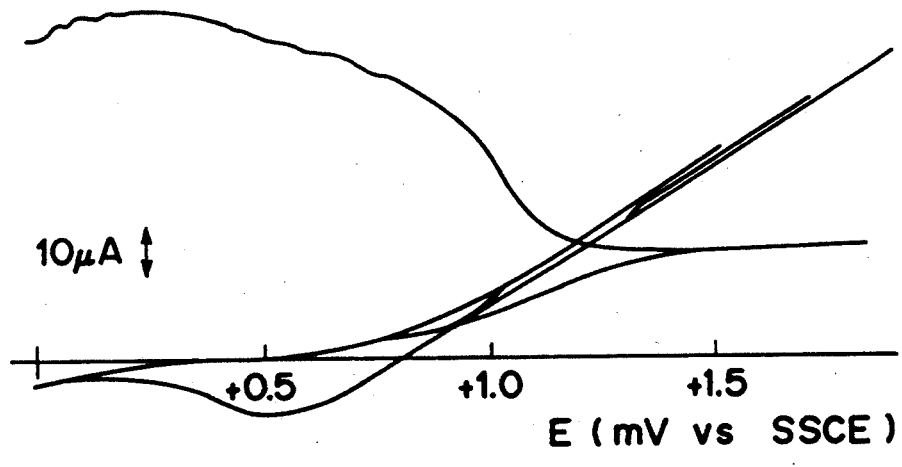
F I G. 2B

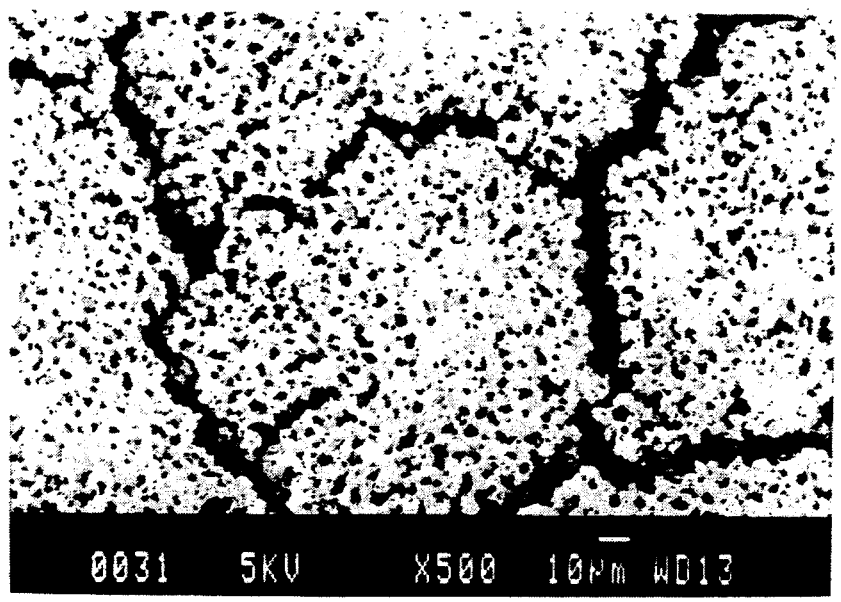
F I G. 3C

ION-SENSITIVE FILM, METHOD OF PRODUCING THE SAME AND ION SENSOR

TECHNICAL FIELD

The present invention relates to an ion sensor, and particularly to a solid film type ion sensor comprising a conductive substrate which is provided with a layer containing a redox responsive substance and a polymeric substance containing and carrying an ion carrier substance.

BACKGROUND ART

It has been proposed to measure an ion concentration by measuring potential response or current response of a carbon material or the like used as a conductive material on which a redox functional layer is coated. However, in this case, the potential or current response of the electrode is generated on the boundary between the different substances. The adhesion between the different substances is therefore a problem. In addition, since an ion concentration is measured in an aqueous solution, differences between the degrees of swelling of the materials used cause the separation of the materials or the occurrence of pin-holes. It is thus difficult to form an ion sensor having stability for a long time.

DISCLOSURE OF THE INVENTION

It is an object of the present invention to solve the problems of prior art and provide an ion sensor having excellent durability, preservative stability and sensor characteristics.

In a conventional method of physically coating a redox manifesting substance and then an ion selective layer (in which an ion selective substance and polyvinyl chloride coexist together) on a conductive material, sensor characteristics with reproducibility cannot be expected because both layers are separated on the boundary therebetween. In the present invention, therefore, in order to solve the problem, an attempt is made to dissolve both substances in a common solvent, e.g., tetrahydrofuran (THF), so that both substances is apparently brought into a compatible system owing to electrolytic reaction.

The ion sensitive film of the present invention comprises a mixed layer containing a redox manifesting substance manifesting the redox function and a polymeric compound containing an ion carrier substance.

The ion sensitive film of the present invention is produced by electrolytic polymerization reaction using a three-pole cell in an electrolyte containing a redox-manifesting substance manifesting the redox function a polymeric compound containing an ion carrier substance to form a mixed layer containing both substances.

An ion sensor of the present invention comprises a conductive substance coated with an ion sensitive layer, wherein the ion sensitive layer comprises a mixed layer containing a redox manifesting substance manifesting the redox function and a polymeric compound containing an ion carrier substance.

The present invention can provide an ion sensor having excellent durability, preservative stability and sensor characteristics.

Specifically, a layer is formed on a conductive substrate by cross matrix polymerization of a redox responsive substance and a polyvinyl chloride layer containing an ion carrier substance by using an electrolytic polymerization process. This layer, the same layer coated on a conductive substance/redox functional layer or the same layer with an ion carrier layer coated thereon exhibits sensor characteristics (the gradient of the Nernst's equation, the response speed and so on) which are the same as those of the layer formed by the conventional method. The layer resistance can be reduced to about half of that of the layer formed by physically bonding layers in the conventional method.

It was also found that, since peeling hardly occurs in the composite layer of the present invention, the sensor exhibits stable electrode potential and good durability.

Further, other objects and effects will be clarified by reading the detailed description below of examples with reference to the the drawings.

BRIEF DESCRIPTION OF THE DRAWINGS

FIG. 1 is a schematic drawing of the structure of an ion sensor in accordance with an example of the present invention;

FIG. 2A is a drawing showing a cyclic voltamograph of simultaneous electrolytic polymerization of 4,4'-biphenol (THF system) and hydrogen ion carriers;

FIG. 2B is a drawing showing a cyclic voltamograph of electrolytic polymerization of 4,4'-biphenol (THF system);

FIG. 3C is a drawing showing a SEM photographic image of a layer surface of Comparative Example 2 and showing that cracks and grains are produced.

BEST MODE FOR CARRYING OUT THE INVENTION

Figure 2C:
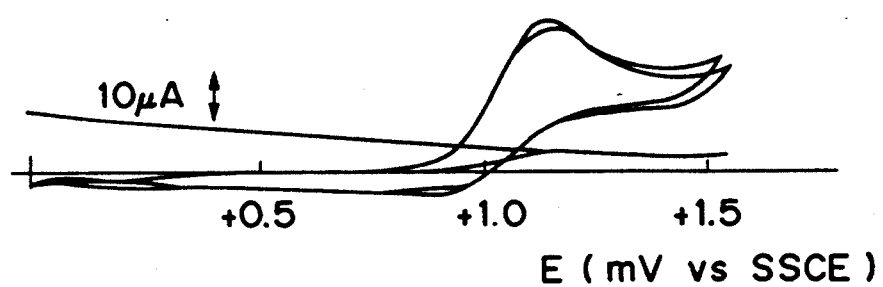
FIG. 2C is a drawing showing a cyclic voltamograph of electrolytic polymerization of 4,4'-biphenol ($CH_3CN$-acetonitrile system)

Examples of the present invention are described below with reference to the attached drawings.

EXAMPLE 1

FIG. 1 is a schematic drawing of the structure of the ion sensor formed in this example.

A lead wire 2 (Uremet wire manufactured by Junko Co., Ltd.) was bonded to one bottom surface 1a of a cylinder 1 of a graphite carbon material (EG-51 manufactured by Nippon Carbon Co., Ltd.) which had a diameter of 1.5 mm and a length of 3 mm by using a conductive adhesive 3 (C-850-6 manufactured by Amicon Co., Ltd.). The cylinder 1 was then inserted into a polyfluoroethylene tube 4 (inner diameter, 1.73 mm) and then insulated by using an insulating adhesive 5 (TB2067 manufactured by Three Bond Co., Ltd.) to form a graphite carbon electrode.

Electrolytic polymerization reaction was made by using a three-pole cell comprising the thus-formed carbon electrode used as a functional electrode, a saturated sodium chloride calomel electrode (SSCE) used as a reference electrode and a platinum net used as a counter electrode under the electrolytic oxidation conditions described below to form a layer 6 containing a p,p'-biphenol polymer serving as a redox manifesting substance and an ion selective component which were combined in a matrix so as to have the characteristics of both substances.

Although 4,4'-biphenol was used as p,p'-biphenol in this example, biphenol is not limited to this.

| (Electrolyte) | |
|---|---|
| Redox manifesting substance: | |
| 4,4'-biphenol | 0.05M |
| Sodium perchlorate | 0.02M |
| Hydrogen ion carrier substance: | |
| Tridodecylamine (TDDA) | 37.5 mg (6.5 wt %) |
| Potassium tetrakis (p-chlorophenyl) borate (KTpClPB) | 4.0 mg (0.7 wt %) |
| Di-(2-ethylhexyl) sebacate (DOS) | 389.38 mg (67.1 wt %) |
| Polyvinyl chloride (PVC) | 149.38 mg (25.7 wt %) |
| Solvent: THF solution | 25 ml |
| Electrolytic polymerization condition: | |
| Controlled potential electrolysis was made for 10 minutes at +1.4 V after three times of sweep within the range of 0.0 to +1.4 volts relative to SSCE (at a sweep rate of 50 mV/second). | |

FIG. 2A shows a cyclic voltamograph during electrolytic polymerization. The results show the tendency that the oxidation current value linearly increases as the oxidation potential (positive potential value) increases after a broad oxidation current peak has appeared. This reveals that the oxidation reaction in the layer is slow reaction and that the electrode reaction determines the lamination rate.

COMPARATIVE EXAMPLE

In Comparative Example 1, electrolytic polymerization was effected in the electrolyte described below containing THF as a solvent and no ion carrier substance.

| (Electrolyte) | |
|---|---|
| Redox manifesting substance: | |
| 4,4'-biphenol | 0.05M |
| Sodium perchlorate | 0.20M |
| Solvent: THF | 25 ml |
| Electrolytic polymerization condition: | |
| Controlled potential electrolytic reaction was made for 10 minutes at +1.4 V after three times of sweep within the range of 0.0 to +1.4 volts (sweep rate of 50 mV/second). | |

As shown in FIG. 2B, the cyclic voltamograph of electrolytic polymerization during lamination shows the same tendency as that shown in Example 1. This reveals that the solvent in the electrolyte significantly contributes to the lamination.

COMPARATIVE EXAMPLE 2

In Comparative Example 2, electrolytic polymerization was made in the electrolyte below containing no ion carrier substance and acetonitrile as a solvent.

| (Electrolyte) | |
|---|---|
| Redox manifesting substance: | |
| 4,4'-biphenol | 0.05M |
| Sodium perchlorate | 0.20M |
| Solvent: acetonitrile | 25 ml |
| Electrolytic polymerization condition: | |
| Controlled potential electrolytic reaction was made for 10 minutes at +1.5 V after three times of sweep within the range of 0.0 to +1.4 volts relative to SSCE (sweep rate of 50 mV/second). | |

As shown in FIG. 2C, a cyclic voltamograph of the layer-coated electrode during the formation thereof shows a clear peak of oxidation current.

Namely, this reveals that the oxidation reaction of the electrolytic polymerization reaction of poly (4,4'-biphenol) in an acetonitrile-NaClO$_4$ system proceeds at a higher rate than that in a THF-NaClO$_4$ system and that the rate of the oxidation reaction is determined by the diffusion of the electrode active substance (monomer).

Figure 3A:
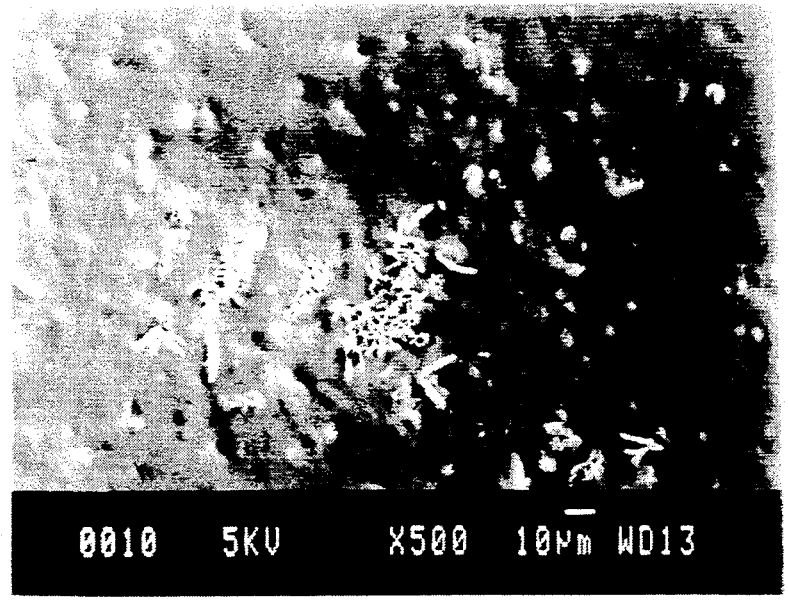
FIG. 3A is a drawing showing a SEM photographic image of a layer surface of Example 1 and showing that pores in a redox manifesting substance are charged with hydrogen ions.
Figure 3B:
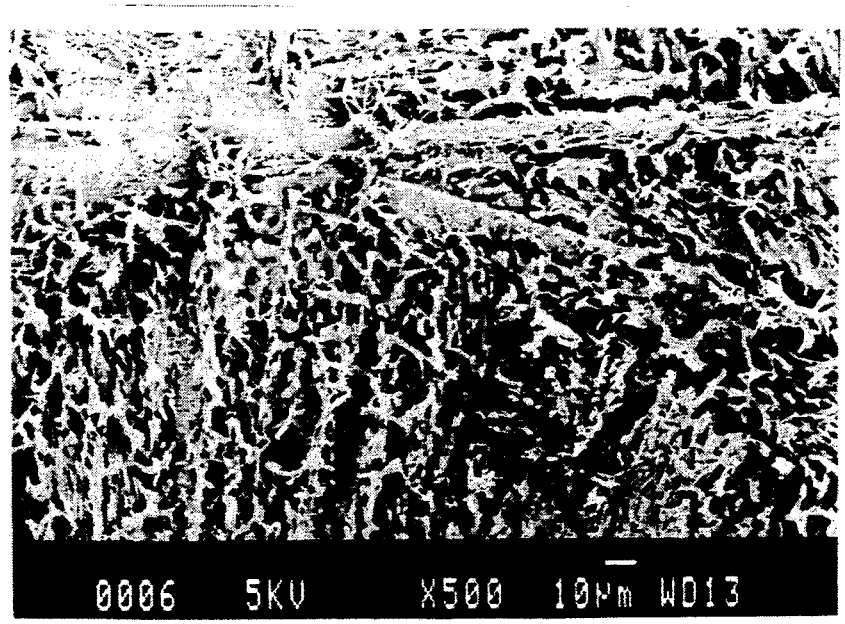
FIG. 3B is a drawing showing a SEM photographic image of a layer surface of Comparative Example 1 and showing that a redox manifesting substance is polymerized, with leaving pores open.

In observation by a scanning electron microscope (SEM), this example shown in FIG. 3A shows that the pores produced in Comparative Example 1 shown in FIG. 3B are charged with the hydrogen ion carrier layer. While cracks and grains are produced in the poly(4,4'-biphenol) layer formed in the acetonitrile-NaClO$_4$ system, as shown in FIG. 3C. Further, the thickness of the electrolytic layer in the acetonitrile-NaClO$_4$ system is several hundreds $\mu$m, while the poly (4,4'-biphenol) layer formed in the THF-NaClO$_4$ system is a thin layer having a thickness of about 60 $\mu$m but a dense and uniform layer.

EXPERIMENTAL EXAMPLE 1

A hydrogen ion carrier layer having the composition below was further coated in a thickness of about 0.8 mm on the layer electrode formed by the method of Example 1 to form a layer electrode.

| (Hydrogen ion carrier composition) | |
|---|---|
| TDDA | 313 mg (6 wt %) |
| KTpClPB | 31.3 mg (0.6 wt %) |
| DOS | 3255 mg (62.3 wt %) |
| PVC | 1625 mg (31.1 wt %) |
| Solvent: THF | |

Plots of pH versus electromotive force of the thus-formed layer electrode at 37°±0.05° C. shows a linear relation with a gradient (referred to as "gradient of calibration curve) of 58.88 mV/pH.

The layer resistance of the layer electrode in a wet state was measured by an a.c. impedance method in accordance with the following method: The layer electrode of this example and a reference electrode (SSCE) were immersed in a 50 mmol/l phosphate buffer, and a potentiostat (manufactured by Hokuto Denko Co., Ltd.: HA.50/G) was connected to a frequency analyzer (2150A model manufactured by Solatron Co., Ltd.). The frequency was changed from 65 kHz to 0.05 kHz at a weep rate of 10 steps per digit. The relation between the current I (A) flowing during application of an a.c. voltage (V) and the impedance Z is expressed by the following formula:

$$Z = \frac{V}{I} = R - j\frac{1}{WC} \quad (1)$$

wherein $j = \sqrt{-1}$.

Figure 4:
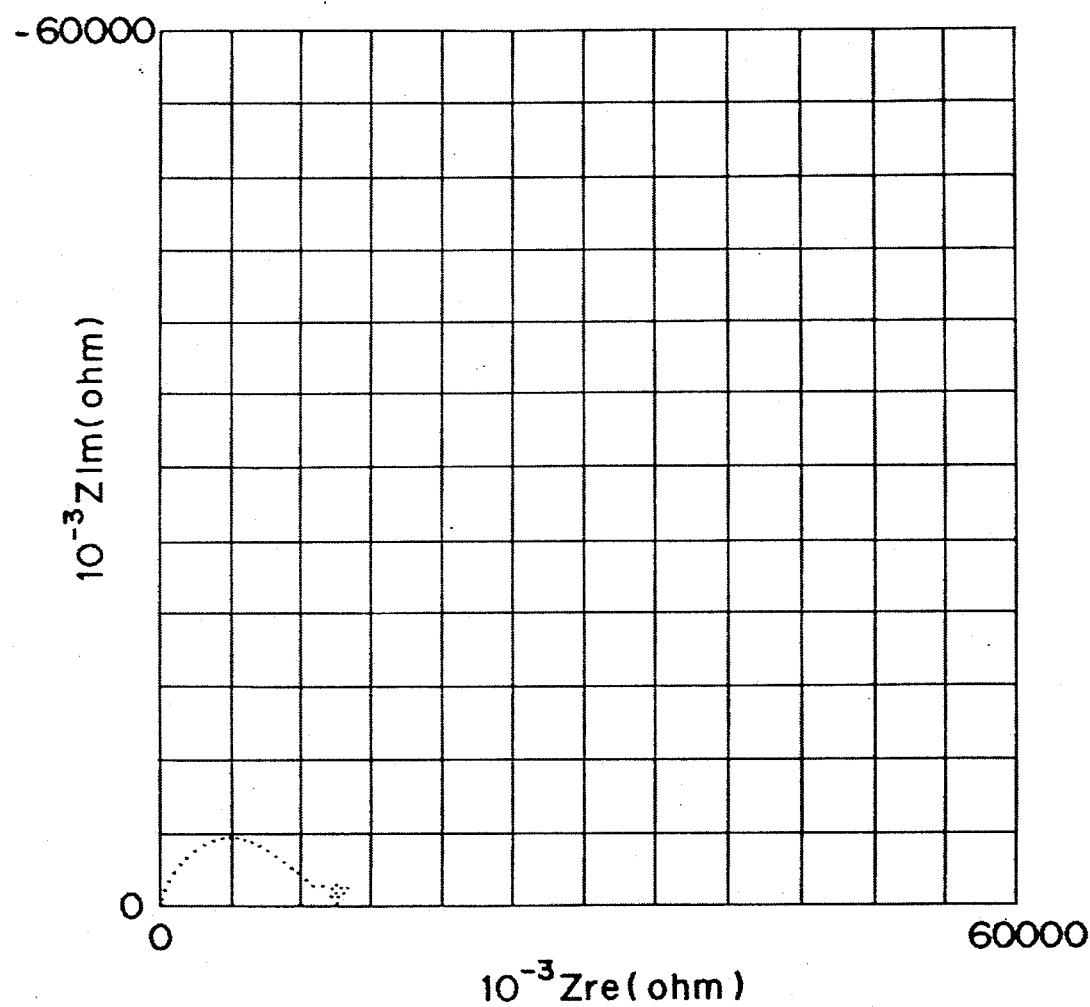
FIG. 4 is a drawing showing Cole-Cole plots of the layer formed in Example 1.

The real portion (R) of the impedance Z obtained by the formula (1) was separated from the imaginary portion (1/WC) thereof, and both portions were plotted on the X- and Y axes, respectively, to form a graph (Cole-Cole plots). An example of the graphs obtained is shown in FIG. 4. Judging from FIG. 4, it is thought that the impedance of the layer electrode formed in this example is equivalent to that of a simple circuit in which a resistance and a capacitor are connected in parallel. The resistance value and the capacity were the following:

$R = 8.08 \, M\Omega$

C (capacity component) $= 1.95 \times 10^{-10}$ F.

EXPERIMENTAL EXAMPLE 2

A layer electrode was formed by coating a poly (4,4'-biphenol) layer in an acetonitrile-NaClO$_4$ system on a carbon electrode, as in Comparative Example 2, and then performing the same experiments as those performed in Experimental Example 1. The electrode resistance of the thus-formed layer electrode was 4.37 M$\Omega$ which was about half of that of the layer electrode formed in Experimental Example 1. The gradient of the calibration curve was 60.31 mV/pH (37°±0.05° C.) which was further close to the theoretical value 61.536 (37° C.).

EXPERIMENTAL EXAMPLE 3

The same hydrogen ion carrier layer as that used in Experimental Example 1 was coated on the surface of the electrolytic polymer layer formed in Comparative Example 1 by employing a dipping method.

The thus-formed electrode comprising the carbon electrode, the (4,4'-biphenol) electrolytic layer and the hydrogen ion carrier layer showed a calibration curve with a gradient of 61.06 mV/pH (37° C.) which was substantially equal to the theoretical value. The layer resistance measured by the same method as that employed in Experimental Example 1 was 11.86 M$\Omega$.

The above-described phenomenon resulted in the following finding: Although the poly (4,4'-biphenol) layer made of the polymerization layer (particularly, CH$_3$CN-NaClO$_4$ system) shows the ideal Nernst potential response, as described above in Experimental Example 3, it has a problem in that the layer resistance is slightly high. While, when the hydrogen ion carrier substance and the electrolytic oxidation substance are caused to coexist together during electrolytic reaction, as in Experimental Examples 1 and 2, since a layer which is apparently crossed and combined with a polymeric matrix is interposed between the electrolytic polymerization layer and the ion carrier layer, it is possible to increase the ion conductivity and the response speed, decrease the layer resistance and maintain the characteristics such as the gradient of the line of the Nernst's relational expression.

COMPARATIVE EXAMPLE 3

Figure 2D:
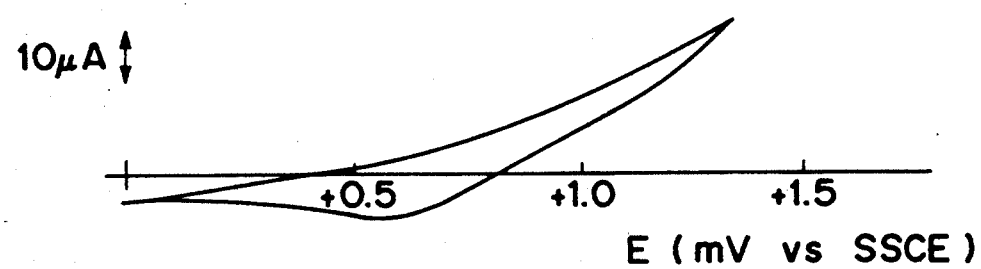
FIG. 2D is a drawing showing a cyclic voltamograph of electrolytic polymerization of 4,4'-biphenol ($CH_3CN$-acetonitrile system) after a hydrogen ion carrier layer has been coated.

A layer having the same hydrogen ion carrier composition as in Experimental Example 1 was coated in a thickness of about 10 μm on a graphite carbon material in the same way as in Example 1. The coated carbon material was then subjected to electrolytic polymerization of 4,4'-biphenol in a NaClO$_4$-CH$_3$CN system, as in Comparative Example 2. In this case, the cyclic voltamograph shown in FIG. 2D was obtained.

EXAMPLE 2

An ion sensor was formed by the same method as in Example 1 with the exception that a potassium ion carrier layer having potassium ion (K+) selectivity and the composition described below was used in place of the hydrogen ion carrier layer.

| (Potassium ion carrier layer composition) | |
| --- | --- |
| Valinomycin | 25 mg |
| KTpClPB | 5 mg |
| DOS | 647 mg |
| PVC | 323 mg |
| Solvent: THF solution | |

EXPERIMENTAL EXAMPLE 4

The characteristic between the electrode potential of the potassium ion sensor formed in Example 2 and log [K+] was measured relative to the reference electrode SSCE within the K+ concentration range of 10$^{-3}$ to 1 (mol/l). A good linear relation was established between the electrode potential and log [K+], and the gradient of the like was 59.78 mV/log [K+] (37°). Substantially no elution of the 4,4'-biphenol polymer layer into the potassium ion carrier layer was observed in this example, and the layer resistance was 8.08 M$\Omega$.

EXAMPLE 3

An ion sensor was formed by the same method as that employed in Example 2 with the exception that a chlorine ion carrier layer having chlorine ion (Cl−) selectivity and composition below was used in place of the hydrogen ion carrier layer.

| (Chlorine ion carrier layer composition) | |
| --- | --- |
| Triphenyltin chloride | 82.7 mg |
| DOS | 725.3 mg |
| PVC | 324.7 mg |
| THF | 10 ml |

EXPERIMENTAL EXAMPLE 5

The characteristic between the electrode potential of the chlorine ion sensor formed in Example 3 and the Cl− ion concentration was measured by using the reference electrode SSCE within the Cl− ion concentration range of 10$^{-3}$ to 10$^{-0.5}$. As a result of the measurement, a good linear relation is established between the electrode potential and log [Cl−], and the gradient of the line was −70.02 mV/log [Cl−] (37° C.±0.05). The layer resistance was 6.07 M$\Omega$. Substantially no elution of the chlorine ion carrier layer was observed in this example, and the strong 4,4'-biphenol polymer layer was coated on the carbon material.

As described above, when a layer is formed on a conductive substrate by cross matrix polymerization of a redox responsive substance and a polyvinyl chloride layer containing an ion carrier substance by an electrolytic polymerization method, when such a layer is formed on a conductive substrate/redox functional layer or when an ion carrier layer is coated on such a layer, the sensor characteristics (the gradient of a calibration curve, the response speed and so on) were the same values as those obtained by the conventional method, and the layer resistance can be decreased to about half of that of the layer formed by physically bonding layers in accordance with the conventional method.

Further, since peeling hardly occurs in such a composite layer, the sensor exhibits extremely stable potentials and has good durability.

Although 4,4'-biphenol is used in the examples, it is obvious to persons skilled in the art that p,p'-biphenol is generally used. It is also obvious that, although the ion sensors for hydrogen ions, potassium ions and chlorine ions are described above are described above, the present invention can be applied to other ion sensors and biosensors.

Other materials which can be used for achieving the present invention will be described below.

Examples of conductive substrates include conductive carbon materials such as basal plane pyrolytic graphite (referred to as "BPG" hereinafter), and glassy carbon; metals such as gold, platinum, copper, silver, palladium, nickel, iron and the like; and particularly noble metals and these metals the surfaces of which are coated with semiconductors such as indium oxide, tin oxide or the like. Of these materials, conductive carbon materials are preferable, and BPG is particularly preferable. The conductive substrate may be also a metal or semiconductor substrate used as a base or combined with a separated gate type of field effect transistor (FET) and then coated with a metal, a metal oxide or a conductive carbon material.

The layer manifesting the redox function has the property of generating a constant potential in the conductive substrate by the redox reaction of the electrode adhering to the surface of the conductive substrate. Particularly, it is preferable that the potential is not changed by the oxygen gas partial pressure. Preferable examples of such redox function-manifesting layers include (1) organic compound films and polymer films which can produce quinone-hydroquinone type redox reaction; (2) organic compound films and polymer films which can produce amine-quinoid type redox reaction; (3) conductive substances such as poly (pyrrole), poly (thienylene) and the like. As an example, in the case of a polymer, the quinone-hydroquinone type redox reaction is expressed by, for example, the following reaction formula:

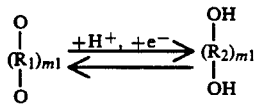

(wherein $R_1$, $R_2$ each denote, for example, a compound having an aromatic group-containing structure).

As an example, in the case of a polymer, the amine-quinoid type redox reaction is expressed by, for example, the following reaction formula:

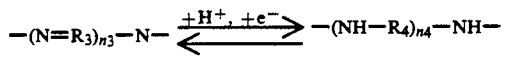

(wherein $R_3$, $R_4$ each denote a compound having, for example, an aromatic group-containing structure).

Examples of redox-manifesting compounds which can form a layer manifesting the redox function include the following compounds (a) to (d):

(a) Hydroxyaromatic compounds expressed by the following formula:

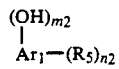

(wherein $Ar_1$ denotes an aromatic nucleus; each $R_5$, a substituent; $m_2$, 1 to the effective valence number of $Ar_1$; and $n_2$, 0 to the effective valence number of $Ar_1 - 1$).

An aromatic nucleus denoted by $Ar_1$ may be a monocyclic nucleus such as a benzene nucleus or the like, or a polycyclic nucleus such as an anthracene nucleus, a pyrene nucleus, a chrysene nucleus, a perylene nucleus, a coronene nuceous or the like. Such an aromatic nucleus may have a benzene skeleton or a heterocyclic skeleton. Examples of substituents $R_5$ include alkyl groups such as a methyl group and the like; aryl groups such as a phenyl group and the like; halogen atoms and the like. Typical examples of such compounds include biphenol, dimethylphenol, phenol, hydroxypyridine, o- or m-benzyl alcohol, o-, m- or p-hydroxybenzaldehyde, o- or m-hydroxyacetophenone, o-, m- or p-hydroxypropiophenone, o-, m- or p-carboxyphenol, diphenylphenol, 2-methyl-8-hydroxyquinoline, 5-hydroxy-1,4-naphtoquinone, 4-(p-hydroxyphenyl) 2-butanone, 1,5-dihydroxy-1,2,3,4-tetrahydronaphthalene, bisphenol A, salicylanilide, 5-hydroxyquinoline, 8-hydroxyquinoline, 1,8-dihydroxyanthraquinone, 5-hydroxy-1,4-naphthoquinone and the like.

(b) Amino aromatic compounds expressed by the following formula:

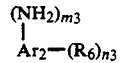

(wherein $Ar_2$ denotes an aromatic nucleus; each $R_6$, a substituent; $m_3$, 1 to the effective valence number of $Ar_2$; and $n_3$, 0 to the effective valence number of $Ar_2 - 1$).

Examples of aromatic nuclei $Ar_2$ and substituents $R_6$ tat may be used include the same as those of the aromatic nuclei $Ar_1$ and the substituents $R_5$, respectively, in compounds (a). Typical examples of amino aromatic compounds include aniline, 1,2-diaminobenzene, aminopyrene, diaminopyrene, aminochrysene, diaminochrysene, 1-aminophenanthrene, 9-aminophenanthrene, 9,10-diaminophenanthrene, 1-aminoanthraquinone, p-phenoxyaniline, o-phenylenediamine, p-chloroaniline, 3,5-dicbloroaniline, 2,4,6-trichloroaniline, N-methylaniline, N-phenyl-p-phenylenediamine and the like.

(c) Quinones such as 1,6-pyrenequinone, 1,2,5,8-tetrahydroxynarzaline, phenanthrenequinone, 1-aminoanthraquinone, purpurin, 1-amino-4-hydroxyanthraquinone, anthrarufin and the like.

Of these compounds, 4,4'-biphenol, 2,6-xylenol, 1-aminopyrene are particularly preferable.

(d) Pyrrole and derivatives thereof (for example, N-methylpyrrole), thiophene and derivatives thereof (for example, methylthiophene) and the like Other examples of compounds manifesting the redox function include compounds having the redox reactivity such as poly(N-methylaniline) [Onuki, Matsuda, Koyama, Nihon Kagakukaishi, 1801–1809 (1984)], poly(2,6-dimethylamine), poly(o-phenylenediamine), poly(phenol), polyxylenol; condensation polymerization quinone-type vinyl polymers such as polymers of pyrazoloquinone vinyl monomers, isoalloxazine-type vinyl monomers and the like, all of which contain any one of the compounds (a) to (d); low-polymerization degree polymers (oiligomers) of the compounds (a) to (d); polymeric compounds such as polyvinyl compounds, polyamide compounds and the like to which the compounds (a) to (d) are respectively fixed. The term "polymers" involves both homopolymers and mutual polymers such as copolymers and the like.

Preferable examples of supporting electrolytes include sodium perchlorate, sulfuric acid, disodium sulfate, phosphoric acid, boric acid, potassium tetrafluorophosphate, quaternary ammonium salts and the like.

Examples of ion carrier substances that may be used in accordance with the test ion include the following substances:

(i) Hydrogen Ion

Examples of hydrogen ion carrier substances that may used include the following substances:
Amines expressed by the following formula:

(wherein $R_7$, $R_8$ and $R_9$ denote the same alkyl group or different alkyl groups, at least two of which are alkyl groups each having 8 to 18 carbon atoms) and compounds expressed by the following formula:

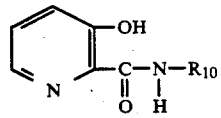

(wherein $R_{10}$ denotes an alkyl group having 8 to 18 carbon atoms).

Of these compounds, tri-n-dodecylamine is preferable, and tridodecylamine is particularly preferable.

(ii) Potassium Ion

Examples of potassium ion carrier substances include valinomycin, nonacutin, monacutin, crown ether compounds Examples of potassium ion carrier substances include valinomycin, nonacutin, monacutin, crown ether compounds such as dicyclohexyl-18-crown-6, naphto-15-crown-5, bis(15-crown-5) and the like. Of these compounds, valinomycin and bis(15-crown-5) are preferable.

(iii) Sodium Ion

Examples of sodium ion carrier substances include aromatic amides and diamides; aliphatic amides and diamides; crown compounds such as bis[(12-crown-4)methyl]dodecylmalonate, N,N,N,N-tetrapropyl-3,6-dioxanate diamide, N,N,N',N'-tetrabenzyl-1,2-ethylenedioxydiacetamide, N,N'-dibenzyl-N'N'-diphenyl-1,2-phenylenediacetamide, N,N',N''-triheptyl-N,N',N''-trimethyl-4,4',4''-propylidyne tris(3-oxabutylamide), 3-methoxy-N,N,N,N-tetrapropyl-1,2-phenylenedioxydiacetamide, (−)-(R,R)-4,5-dimethyl-N,N,N,N-tetrapropyl-3,6-dioxaoctanediamide, 4-methyl-N,N,N,N-tetrapropyl-3,6-dioxaoctanediamide, N,N,N,N-tetrapropyl-1,2-phenylenedioxydiacetamide, N,N,N,N-tetrapropyl-2,3-naphthalenedioxydiacetamide, 4-t-butyl-N,N,N,N-tetrapropyl-1,2-cyclohexanedioxydiacetamide, cis-N,N,N,N-tetrapropyl-1,2-cyclohexanedioxydiacetamide, trans-N,N,N,N-tetrapropyl-1,2-cyclohexanedioxydiacetamide and the like. Of these compounds, bis[(12-crown-4)methyl]dodecylmalonate is preferably used.

(iv) Chlorine Ion

Examples of chlorine ion carrier substances include quaternary ammonium salts expressed by the following formula:

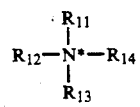

(wherein $R_{11}$, $R_{12}$ and $R_{13}$ denote the same or different alkyl groups each having 8 to 18 carbon atoms, and $R_{14}$ denotes hydrogen or an alkyl group having 1 to 8 carbon atoms) and triphenyltin chloride expressed by the following formula:

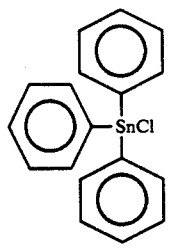

(v) Calcium Ion

Calcium bis[di-(n-octylphenyl) phosphate], (−)-(R,R)-N,N-bis[(11-ethoxycarbonyl)undecyl]-N,N',4,5-tetramethyl-3,6-dioxaoctanediamide, calcium bis[di(n-decyl) phosphate] and the like are preferably used.

(vi) Bicarbonate Ion

Examples include quaternary ammonium salts expressed by the following formula:

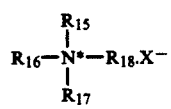

(wherein $R_{15}$, $R_{16}$ and $R_{17}$ denote the same or different alkyl groups each having 8 to 18 carbon atoms, $R_{18}$ denotes a hydrogen atom or an alkyl group having 1 to 4 carbon atoms, and X denotes Cl-, Br- or OH-);

tertiary amine compounds expressed by the following formula:

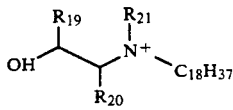

(wherein $R_{19}$ denotes a phenyl group, a hydrogen atom or a methyl group, $R_{20}$ denotes a hydrogen atom or a methyl group, and $R_{21}$ denotes a hydrogen atom, a methyl group or an octadecyl group); and compounds expressed by the following formula:

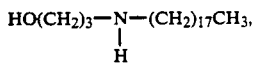

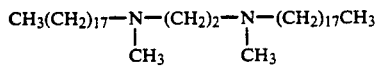

(vii) Ammonium Ion

Nonacutin, monacutin and tetranacutin are preferably used.

Examples of electrolyte salts include sodium tetrakis(p-chlorophenyl) borate, potassium tetrakis(p-chlorophenyl) borate and compounds expressed by the following formula:

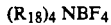

(wherein $R_{18}$ denotes an alkyl group, preferably an alkyl group having 2 to 6 carbon atoms).

Of these compounds, potassium tetrakis(p-chlorophenyl) borate is preferable for hydrogen ions, potassium ions, sodium ions and bicarbonate ions, tetrachloroborate is preferable for chlorine ions, and di-(n-octylphenyl) phosphate is preferable for calcium ions.

Examples of polymers used as a layer material for carrying an ion carrier substance include organic polymers such as vinyl chloride resins, vinyl chloride-ethylene copolymers, polyesters, polyacrylamides, polyurethanes and the like; and inorganic polymers such as silicone resins and the like. Vinyl chloride among these compounds is preferable.

A plasticizer which is not easily eluted is used. Examples of such plasticizers include dioctyl sebacate, dioctyl adipate, dioctyl maleate, di-n-octylphenyl phosphate and the like. Of these plasticizers, dioctyl sebacate (DOS) and di(2-ethylhexyl) sebacate are preferable.

Examples of solvents that may used include acetonitrile, water, dimethylformamide, dimethylsulfoxide, propylenecarbonate methanol and the like. Tetrahydrofuran (THF) is particularly preferable.

The mixed layer used in the present invention can be impregnated with an electrolyte. Examples of such electrolytes include phosphoric acid, dipotassium hydrogen phosphate, sodium perchlorate, sulfuric acid, tetrafluoroborate, tetraphenyl borate and the like. The mixed layer is impregnated with an electrolyte by a simple method of forming the mixed layer and then immersing it in an electrolyte solution.

Any change, modification and addition can be made within the scope of the claims.

What is claimed is:

1. An ion sensitive film comprising a mixed layer containing a polymerized biphenol having a redox function and a polymeric compound containing an ion carrier substance.

2. A method of producing an ion sensitive film comprising a step of forming a mixed layer containing a polymerized biphenol having a redox function and a polymeric compound containing an ion carrier substance by electrolytic polymerization using a three-pole cell in an electrolyte containing a biphenol and the ion carrier substance.

3. An ion sensor comprising a conductive substrate and an ion sensitive layer covering a surface of the conductive substrate, wherein said ion sensitive layer comprising a mixed layer containing a polymerized biphenol having a redox function and a polymeric compound containing an ion carrier substance.

4. An ion sensitive film consisting essentially of an admixture of a redox substance having a redox function and a polymeric compound containing an ion carrier substance.

5. An ion sensitive film according to claim 4, wherein said ion sensitive film is an electrolytically polymerized film.

6. An ion sensitive film according to claim 5, wherein said redox substance is an electrolytically polymerized biphenol.

7. A method of producing an ion sensitive film comprising the steps of:

preparing an electrolyte containing a redox substance and an ion carrier substance; and electrolytically polymerizing by using a three-pole cell in said electrolyte to form the ion sensitive film.

8. A method according to claim 7, wherein said redox substance is biphenol.

9. An ion sensor comprising a conductive substrate and an ion sensitive layer covering a surface of the conductive substrate, wherein said ion sensitive layer consists essentially of an admixture of a redox substance having a redox function and a polymeric compound containing an ion carrier substance.

10. An ion sensor according to claim 9, wherein said ion sensitive film is an electrolytically polymerized film.

11. An ion sensor according to claim 10, wherein said redox substance is an electrolytically polymerized biphenol.

* * * * *

UNITED STATES PATENT AND TRADEMARK OFFICE
CERTIFICATE OF CORRECTION

PATENT NO. : 5,190,636

DATED : March 2, 1993

INVENTOR(S) : Norihiko USHIZAWA ET AL

It is certified that error appears in the above-identified patent and that said Letters Patent is hereby corrected as shown below:

In Column 3, line 44, delete "nc" and insert -- no --.

In Column 8, line 55, delete "3,5-dicbloroaniline" and insert -- 3,5-dichloroaniline --.

Signed and Sealed this

Twenty-third Day of November, 1993

Attest:

BRUCE LEHMAN

Attesting Officer     Commissioner of Patents and Trademarks